United States Patent
Sirimanne et al.

[11] Patent Number: 6,136,014
[45] Date of Patent: Oct. 24, 2000

[54] PERCUTANEOUS TISSUE REMOVAL DEVICE

[75] Inventors: D. Laksen Sirimanne, Palo Alto; Douglas S. Sutton, Pacifica; Natalie V. Fawzi, Belmont, all of Calif.

[73] Assignee: Vivant Medical, Inc., Portola Valley, Calif.

[21] Appl. No.: 09/145,487

[22] Filed: Sep. 1, 1998

[51] Int. Cl.$^7$ ..................................................... A61B 17/34
[52] U.S. Cl. ........................... 606/185; 606/170; 606/172
[58] Field of Search ........................... 606/185, 170–184, 606/113, 127, 128, 129, 200; 604/22–24

[56] References Cited

U.S. PATENT DOCUMENTS

| | | |
|---|---|---|
| Re. 34,056 | 9/1992 | Lindgren et al. . |
| 1,995,725 | 3/1935 | Wappler . |
| 3,174,851 | 3/1965 | Buehler et al. . |
| 3,351,463 | 11/1967 | Rozner et al. . |
| 3,753,700 | 8/1973 | Harrison et al. . |
| 3,989,038 | 11/1976 | Neward . |
| 4,116,198 | 9/1978 | Roos . |
| 4,311,143 | 1/1982 | Komiya . |
| 4,362,160 | 12/1982 | Hiltebrandt . |
| 4,493,320 | 1/1985 | Treat . |
| 4,643,187 | 2/1987 | Okada . |
| 4,657,018 | 4/1987 | Hakky . |
| 4,699,154 | 10/1987 | Lindgren . |
| 4,718,419 | 1/1988 | Okada . |
| 4,811,733 | 3/1989 | Borsanyi et al. . |
| 4,905,691 | 3/1990 | Rydell . |
| 4,921,479 | 5/1990 | Grayzel . |
| 4,935,025 | 6/1990 | Bundy et al. . |
| 4,944,308 | 7/1990 | Åkerfeldt . |
| 4,953,558 | 9/1990 | Akerfeldt . |
| 5,064,424 | 11/1991 | Bitrolf . |
| 5,078,716 | 1/1992 | Doll . |
| 5,080,660 | 1/1992 | Buelna . |
| 5,085,659 | 2/1992 | Rydell . |
| 5,100,423 | 3/1992 | Fearnot . |
| 5,111,828 | 5/1992 | Kornberg et al. . |
| 5,158,545 | 10/1992 | Trudell et al. . |
| 5,171,255 | 12/1992 | Rydell . |
| 5,183,464 | 2/1993 | Dubrul et al. . |
| 5,197,484 | 3/1993 | Kornberg et al. . |
| 5,201,756 | 4/1993 | Horzewski et al. . |
| 5,209,749 | 5/1993 | Buelna . |
| 5,217,458 | 6/1993 | Parins . |
| 5,254,105 | 10/1993 | Haaga . |
| 5,312,417 | 5/1994 | Wilk . |
| 5,353,804 | 10/1994 | Kornberg et al. . |
| 5,417,697 | 5/1995 | Wilk et al. . |
| 5,431,676 | 7/1995 | Dubrul et al. . |
| 5,437,665 | 8/1995 | Munro . |
| 5,454,790 | 10/1995 | Dubrul . |
| 5,480,397 | 1/1996 | Eggers et al. . |
| 5,496,314 | 3/1996 | Eggers . |
| 5,505,728 | 4/1996 | Ellman et al. . |
| 5,526,822 | 6/1996 | Burbank et al. . |
| 5,527,332 | 6/1996 | Clement . |
| 5,569,244 | 10/1996 | Hahnen . |

(List continued on next page.)

OTHER PUBLICATIONS

"Line of Minimally Invasive Biopsy Devices added to HSCA–U.S. Surgical Agreements", Hospital Materials Management, No. 7, vol. 23, Jul. 1, 1998 (no author cited).
"FDA Gives OK to USS Breast–Biopsy System", Medical Industry Today, Dec. 12, 1997 (no author cited).
Imagyn Surgical Product Literature, SITESELECT Stereotactic Breast Biopsy System, (including article entitled: Breast Disease: Assessment and Management of Breast Complaints, Spring 1995 (no author cited).

*Primary Examiner*—Michael Buiz
*Assistant Examiner*—Lien Ngo
*Attorney, Agent, or Firm*—Morrison & Foerster LLP

[57] ABSTRACT

This is a device for percutaneous tissue sampling or excision. In particular, it uses a rotating cutter which produces a helically cut, discrete tissue mass that is removable through a comparatively much smaller access member. The tissue mass is easily reconstructed to its original form and orientation once taken from the body for further study.

46 Claims, 14 Drawing Sheets

U.S. PATENT DOCUMENTS

| | | |
|---|---|---|
| 5,578,030 | 11/1996 | Levin . |
| 5,593,406 | 1/1997 | Eggers et al. . |
| 5,611,798 | 3/1997 | Eggers . |
| 5,647,867 | 7/1997 | Neuberger et al. . |
| 5,707,359 | 1/1998 | Bufalini . |
| 5,709,697 | 1/1998 | Ratcliff et al. . |
| 5,733,283 | 3/1998 | Malis et al. . |
| 5,741,271 | 4/1998 | Nakao et al. . |
| 5,743,906 | 4/1998 | Parins et al. . |
| 5,759,187 | 6/1998 | Nakao et al. . |
| 5,769,086 | 6/1998 | Ritchart et al. . |
| 5,775,333 | 7/1998 | Burbank et al. . |
| 5,782,775 | 7/1998 | Milliman et al. . |
| 5,782,840 | 7/1998 | Nakao . |
| 5,795,308 | 8/1998 | Russin . |
| 5,823,971 | 10/1998 | Robinson et al. . |
| 5,882,316 | 3/1999 | Chu et al. . |

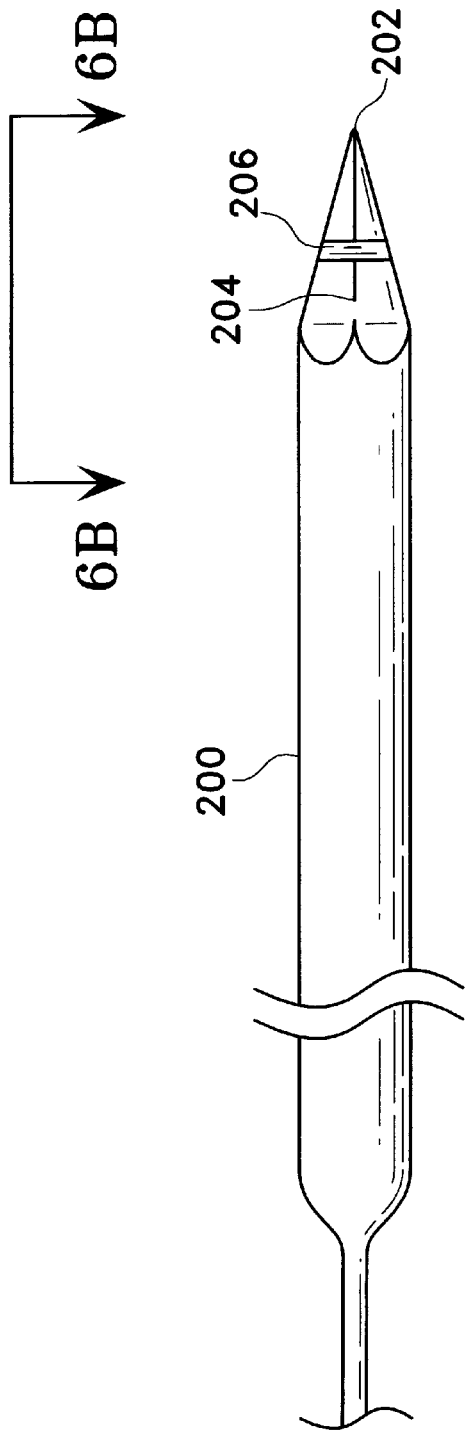
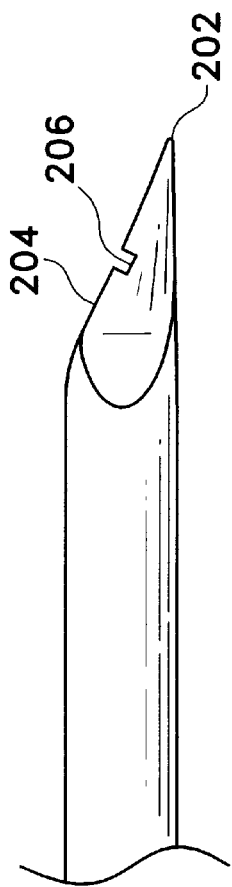
Fig. 6A
Fig. 6B

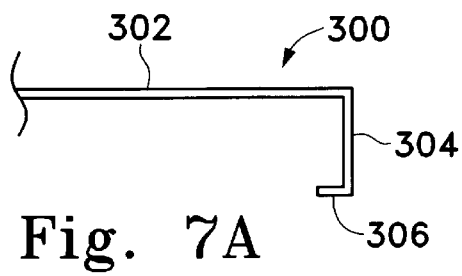
Fig. 7A
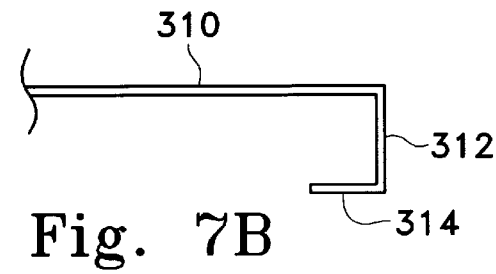
Fig. 7B
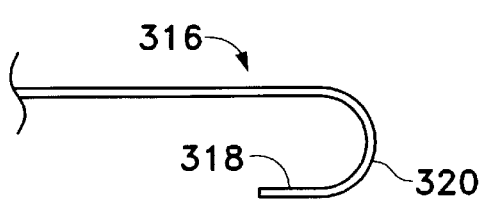
Fig. 7C
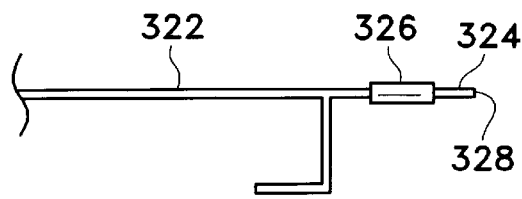
Fig. 7D

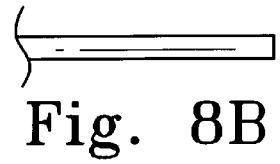
Fig. 8B
Fig. 9A
Fig. 10A
Fig. 11A
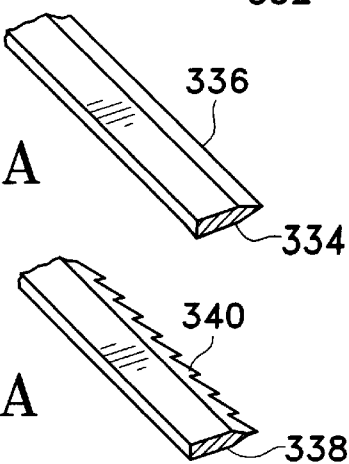
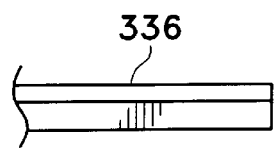
Fig. 9B
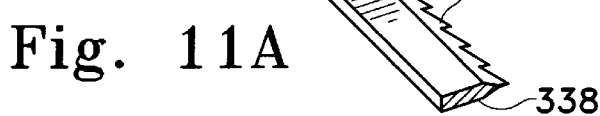
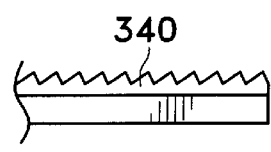
Fig. 10B
Fig. 11B

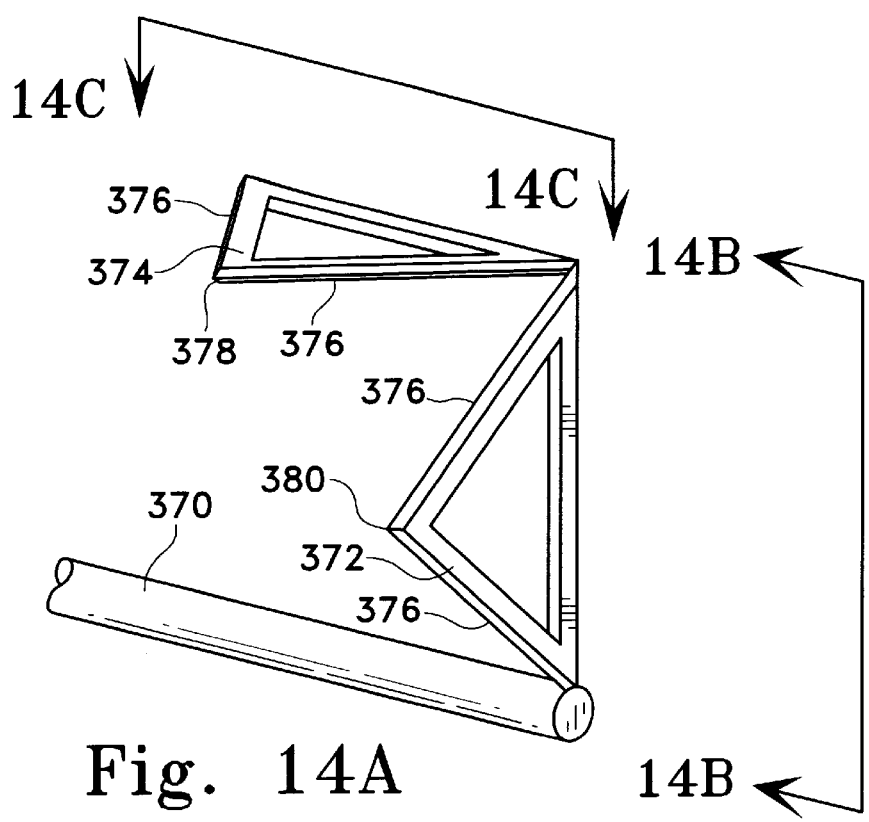
Fig. 14A
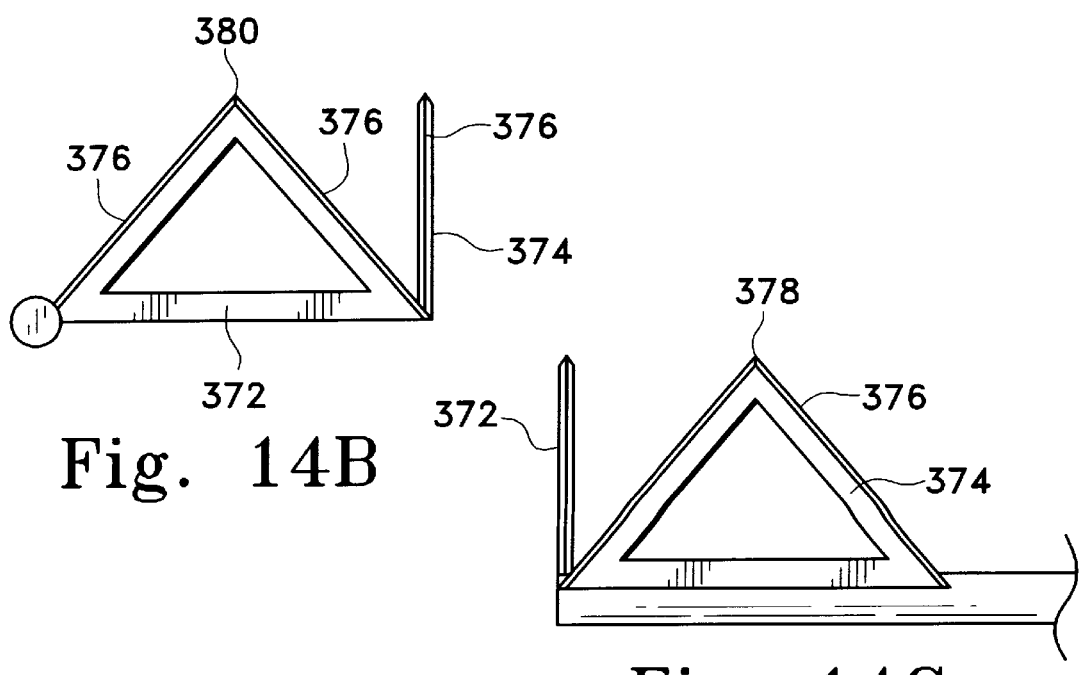
Fig. 14B
Fig. 14C

PERCUTANEOUS TISSUE REMOVAL DEVICE

FIELD OF THE INVENTION

This invention relates to a device and to a related procedure for percutaneous tissue sampling or excision. In particular, it uses a rotating cutter which produces a helically cut, discrete tissue mass that is removable through a comparatively much smaller tissue access device. The tissue mass is easily reconstructed to its original form and orientation once taken from the body for further study.

BACKGROUND OF THE INVENTION

Despite the advances made in technologies such as medical imaging to assist the physician in early stage diagnosis and treatment of patients with possible atypical tissue such as cancer, it is still often necessary to sample difficult-to-reach organ or tissue lesions by biopsy to confirm the presence or absence of abnormalities or disease.

A disease for which biopsy is a critical tool is breast cancer. This affliction is responsible for 18% of all cancer deaths in women and is the leading cause of death among women aged 40 to 55. As with many diseases and other types of cancer, early detection and diagnosis of breast cancer is critical in providing the best chance of survival.

In the majority of cases, detection of the disease is first made when a patient discovers a palpable mass through self-examination and consults her physician. For breast lesions that are more difficult or impossible to detect through palpation, diagnostic techniques such as x-ray mammography and, more recently, digital mammography, and scintimammography are invaluable. Other techniques such as ultrasound, magnetic resonance, the Dilon gamma camera, position emission tomography, MIBI, computed topography, fluoroscopy, thermography, transillumination and diaphanography can also be used to help determine the presence and nature of suspect tissue.

Of these technologies, the primary clinical diagnostic tool for the detection of breast cancer is x-ray mammography. Over 15 million mammograms are performed each year in the United States alone. Mammography uses x-rays to image breast tissue, identifying areas of high density as possible lesions.

Unfortunately, the limitations of technologies such as mammography in accurately detecting precancerous or cancerous lesions in the breast are significant. Among these limitations is the fact that only one out of every five lesions discovered through x-ray mammography proves to be cancerous. Roughly 25% of women have dense breast tissue, which is notoriously difficult to inspect via mammography. Also, mammography is generally less effective for women under 40 years of age. For younger women, therefore, self-examination for palpable lesions or ultrasound examination is important. However, neither of these techniques is able to detect microcalcifications, important possible precursors to cancer.

As long as there is a degree of uncertainty associated with these various diagnostic techniques, biopsies must be performed to sample the suspicious tissue to determine its exact nature and pathology.

In the detection and treatment of breast cancer, there are two general classes of biopsy: the minimally invasive percutaneous fine or core needle biopsy and the more invasive surgical or "open" biopsy.

Open biopsies, both incisional and excisional, are advisable when suspicious lumps should be removed in their entirety or when core needle biopsies don't give complete information about the nature of the lesion.

One such type of open biopsy is the wire localization biopsy. Such a procedure includes the following steps: first, a radiologist inserts a wire into the breast under x-ray guidance to mark the location of the suspect tissue. The tissue is then removed by a surgeon for examination by a pathologist. Although large tissue samples are removed by this technique, the risk of permanent disfigurement, the attendant morbidity and mortality risks associated with surgery, and long hospital recovery times are but three of the many disadvantages associated with open surgical biopsies.

Of the less invasive class of percutaneous biopsies, the least invasive is known as a fine needle biopsy. For palpable lumps, a physician inserts a needle and syringe directly into the lump to obtain a cell sample, which is then examined by a cytologist. For non-palpable lesions identified by x-ray mammography or other diagnostic tool, fine needle biopsies are often performed under stereotactic or ultrasonic guidance. Here, multiple mammograms are taken of the breast and the images are analyzed by a computer to determine the location of the suspect lesion in three dimensions. The physician then penetrates the breast with a needle, targeting the suspect region and removing a small number of cells. There are two significant drawbacks to fine needle biopsy techniques: first, several specimens must be taken to ensure the lesion is well-sampled. Secondly, the limited size of the specimens obtained under fine needle biopsy dictate that a skilled cytologist be involved to analyze the suspect cells out of context of the surrounding healthy tissue.

A second type of percutaneous needle biopsy used to obtain a larger specimen is known as a core biopsy. With this procedure, a larger needle is inserted into the breast via an incision in the skin under stereotactic or ultrasonic guidance. A spring-loaded device is then fired into the breast to obtain a single core sample of tissue, preferably through the center of the lesion. The larger specimen size (up to 20 mm in diameter) obtained by this technique can be more accurately read by a pathologist, who can analyze the suspect cells in the context of the surrounding tissue. Examples of such devices are described in U.S. Pat. No. Re. 34,056 and U.S. Pat. Nos. 4,944,308 and 4,953,558.

Traditionally, as with fine needle biopsies, core biopsies require multiple core samples, typically four to twenty, to ensure an accurately representative sample of the suspect region is profiled. This means that as many as twenty separate needle insertions must be made into the breast through the skin.

More recently developed needle biopsy technologies are directed to solving this problem by allowing multiple samples to be obtained through a single incision, such as that described in U.S. Pat. Nos. 5,709,697 and 5,782,775. One such technology, described in U.S. Pat. Nos. 5,526,822, 5,769,086, and 5,775,333, utilizes a trocar-tipped probe which is positioned in the breast under stereotactic or ultrasonic guidance to align the suspect lesion with an aperture that extends along a specified length of the probe. The tissue is then aspirated into the aperture wherein a rotating cutter in the probe is advanced distally to cut and capture tissue specimen into the probe lumen. The cutter is then withdrawn, transporting the specimen to a tissue collection chamber. Next, the probe, which is still in the breast, is radially rotated in position through a desired angle to align the aperture with another target tissue area. The steps of rotation, cutting, and collection, which can be automated and assisted by vacuum, are repeated until the desired number of samples is obtained.

Although this type of device requires only a small, single incision to obtain a number of core samples, each sample is still limited in size, requiring excision of multiple specimens for accurate pathologic diagnosis. As with other percutaneous excisional devices in which multiple specimens must be obtained, it is often difficult to reconstruct the spatial location and orientation of the suspect tissue as it resided in the breast prior to excision, resulting in a concomitantly difficult pathological analysis.

Another type of percutaneous excisional breast biopsy device designed to first separate healthy tissue from suspect tissue prior to obtaining a single suspect tissue sample is generally described in U.S. Pat. Nos. 5,111,828, 5,197,484, and 5,353,804. This device, however, requires the use of a relatively large diameter cannula to obtain an adequate specimen size.

What is needed is a small-diameter percutaneous excisional biopsy device that allows a physician to obtain, in a minimally invasive manner, a relatively large tissue specimen through a small incision. Further, what is needed is a device that can obtain a specimen large enough for a complete, accurate and satisfactory pathologic determination, obviating the need for obtaining multiple core specimens and reconstructing them ex vivo.

SUMMARY OF THE INVENTION

This invention relates to devices and procedures for removing integral volumes of tissue via percutaneous access. The diameter of the volume removed using this invention is typically larger than the diameter of the access device. Depending upon the size of the device selected, the inventive device may be used for biopsy samples or for excision of larger amounts of tissue containing "suspicious areas" or tumorous masses. The tissue mass removed is typically continuous in form. Because of the method in which the device operates, the trauma caused by removal of the chosen volume is significantly lessened as compared to other available devices. The tissue mass removed is readily reassembled into a discrete mass which has the same form and orientation as the mass had in the body.

The procedure involved the steps of selecting a target tissue mass. A trocar, tubular vessel removal member, and a cutting member are introduced percutaneously to the vicinity of the volume to be removed. The cutting member is positioned so that, as it is advanced and turned (after the trocar is removed), the cutting member produces a generally cylindrical mass of tissue having a circular cut at the front and back end of the cylinder and a spiral cut through the cylinder. The spiral-cut cylinder may be removed after the cutting is completed or during the step of producing that spiral cut. The spirally cut tissue is preferably then reformed into its initial cylindrical shape for further analysis or pathology. The step of cutting may be variously by by the use of RF, ultrasound, or by the use of mechanical cutters, or by combinations of the three.

This procedure may be used in any internal, preferably soft, tissue, but is most useful in breast tissue, lung tissue, prostate tissue, lymph gland tissue, etc. Obviously, though, treatment and diagnosis of breast tissue problems forms the central theme of the invention.

The components typically used in the inventive procedure include a tissue removal member typically having two lumens. The larger lumen is for the removal of excised tissue from the targeted body site and the smaller lumen, which need not be continuous but may be simply a positioner loop or the like, is used for positioning of the cutting member. A trocar fits within the larger lumen in the tissue removal member and is used to penetrate the skin and tissue and thereby to position the distal end of the tubular tissue removal member in the vicinity of the tissue volume to be removed.

The cutting member has a long shaft that typically is placed within the smaller lumen of the tissue removal member. The cutting member is both advanced and rotated so that a generally cylindrical mass of tissue is produced at the chosen site. The lesion or tumor "suspicious mass" is to be situated within that chosen cylindrical region.

The tissue, while it is being cut from or after it has been cut loose from the body by the cutting member is then removed through the large lumen of the tissue removal member, perhaps using an auger-like device to carry the tissue sample to a external collector. Desirably, the removed tissue is placed in sample receptacle for later study.

Generally, the region to be excised is identified using stereotactic indexing apparatus as is well known in the art. It is typical that the rotation and advancement of the cutting member is controlled using an automated controller box.

BRIEF DESCRIPTION OF THE DRAWINGS

FIG. 6A shows a top view; FIG. 6B shows an end view; and FIG. 6C shows a side view of a trocar which fits within the tissue removal member and supports the tissue cutting member as it is introduced into the target tissue region.

FIGS. 7A to 7D show variations of the shape of tissue cutter.

FIGS. 8A to 11B show, variously, front quarter views and top views of configurations of the cutting members shown in FIGS. 7A to 7D.

FIG. 14A shows a front quarter view, FIG. 14B shows an end view, and FIG. 14C shows a side view of mechanical cutting member.

DESCRIPTION OF THE INVENTION

As noted above, this invention relates to devices and procedures for removing integral volumes of tissue, typically breast tissue, via percutaneous access. The diameter of the tissue volume removed using this invention is larger than the diameter of the access device. Depending upon the size of the device selected, the inventive device may be used for biopsy samples or for excision of larger amounts of tissue containing "suspicious areas" or tumorous masses. Because of the method in which the device operates, the trauma caused by removal of the chosen volume is significantly lessened as compared to other available devices. In addition, the tissue mass removed can be readily assembled, after exit from the body, into a discrete mass that has the same form and orientation as the mass had in the body.

In general, the procedure involved is this: first, a target tissue mass is selected. A trocar, tubular vessel removal member, and a cutting member are assembled and introduced percutaneously to the vicinity of the volume to be removed. The cutting member is positioned so that, as it is advanced and turned (after the trocar is removed), the cutting member produces a generally cylindrical mass of tissue having a circular cut at the front and back end of the cylinder and a spiral cut through the cylinder. The spiral cut cylinder may be removed as a continuous strip after the cutting is completed or during the step of producing that spiral cut. The spirally cut tissue is preferably then reformed into its initial cylindrical shape for further analysis or pathology. The step of cutting may be variously by the use of RF, ultrasound, or by the use of mechanical cutters.

Figure 1:
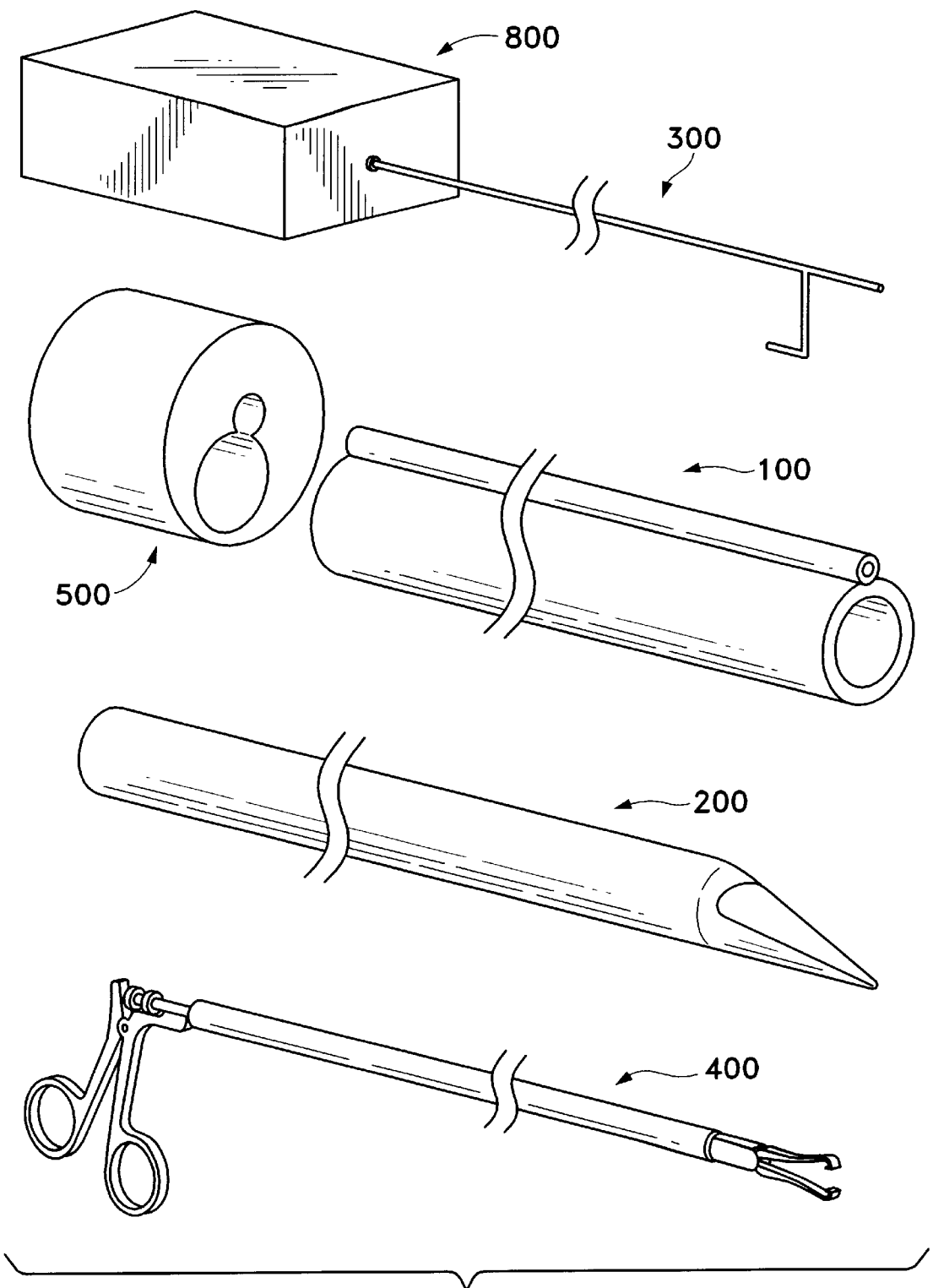
FIG. 1 shows an assemblage of the components, as in a kit, which make up the inventive tissue removal device.

FIG. 1 shows, in generic fashion, the components typically used in the inventive procedure. Tissue removal member (100) is shown in FIG. 1 as typically having two lumens. The larger lumen is for the removal of excised tissue from the targeted body site and the smaller lumen is used for positioning of the cutting member (300), as will be discussed below. The trocar (200), which fits within the larger lumen in tissue removal member (100), is also shown. Trocar (200) is used to penetrate the skin and tissue and thereby to position the distal end of the tubular tissue removal member (100) in the region of the tissue volume to be removed.

FIG. 1 shows a typical cutting member (300). Cutting member (300) has a long shaft that typically is placed within the smaller lumen of tissue removal member (100). When the cutting member (100) shaft is situated in the smaller lumen of tissue removal member (300), it is both advanced and rotated so that a cylindrical mass of tissue is produced at the chosen site. The lesion or tumor is to be situated within that chosen cylindrical region.

The tissue, while or after it has been cut loose from the body by cutting member (300), is then removed, e.g., by a removal member (400) such as that shown in FIG. 1. Desirably, the removed tissue is placed in sample receptacle (500) for later study.

Generally, the region to be excised is identified using stereotactic indexing apparatus as is well known in the art. It is typical that the rotation and advancement of the cutting member (300) is controlled using a controller box (600) such as that depicted in FIG. 1.

TISSUE REMOVAL MEMBER

Figure 2A:
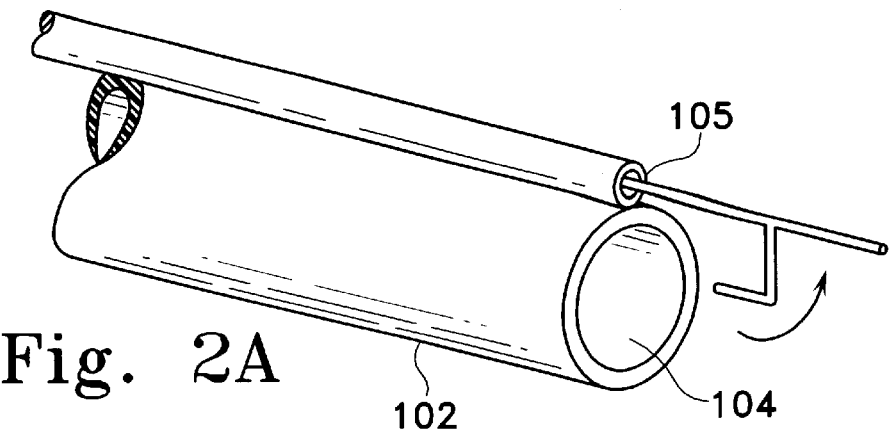
FIGS. 2A to 2D show variations of the tissue removal member and their relation to the rotatable cutting member.

FIG. 2A shows a typical variation of the inventive tissue removal member (102). This variation includes a larger lumen (104) and a smaller lumen (106) which is exterior to large lumen (104). For purposes of illustration only, a cutting member (108) is shown in small lumen (106). Central to this invention is the concept that as the cutting member (108) is rotated by the physician user, it cuts a disc (or spiral as it is advanced) which is significantly larger in diameter than is the large lumen (104) of the tissue removal member (102). Typically, tissue removal member (104) is constructed from any of a large number of polymers typically used in this service, e.g., Nylons, reinforced Nylons, polyethylene, polypropylene, polyethyleneterephthalate (PET), fluorocarbon plastics (e.g., Teflon), etc. The polymers may be reinforced by fibers or filled. As will also be discussed below, the tissue removal member member may be reinforced or made radially expandable using using coils or braids of metals, alloys, or polymers (natural or synthetic) included in the walls of the member. The walls may be made at least partially radio-opaque by introduction of, e.g., powdered tantalum, powdered tungsten, bismuth carbonate, and other known particulate and fibrous radio-opacifiers.

Figure 2B:
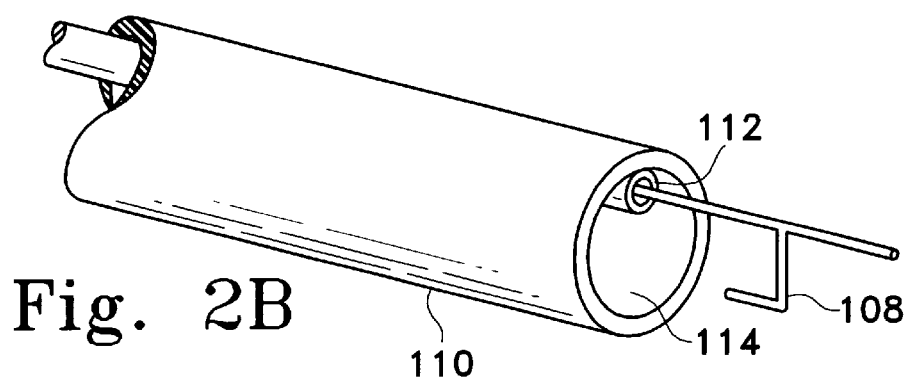

FIG. 2B shows a similar tissue removal member (110). In this variation, the small lumen tubular portion (12) is not exterior to the member (110) but is instead within the large lumen (114). Again, the rotating end rotatable cutting member (108) is shown positioned in the small lumen tubular member (112). This variation has the obvious benefit of being somewhat smaller in overall diameter than is the variation shown in FIG. 2A. However, the size of the cylinder which can be produced by the properly sized cutting member (108) is also somewhat smaller. This variation might, for instance, be better suited for gathering a biopsy sample.

Figure 2C:
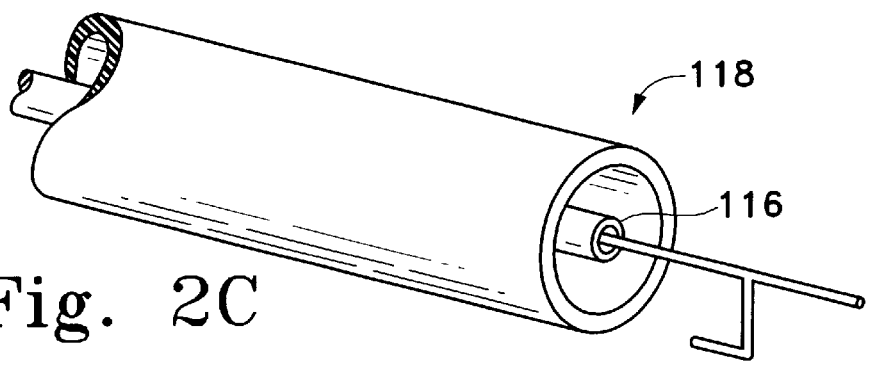

FIG. 2C shows another variation in which the small lumen portion (116) of the tissue removal member (118) is spaced away from the interior wall of the large lumen. This variation is especially suitable for use with the helical tissue removal auger which is discussed in significantly more detail below. It is also especially suitable for use with cutting members which expand or extend outwardly from that small lumen (116).

Figure 2D:
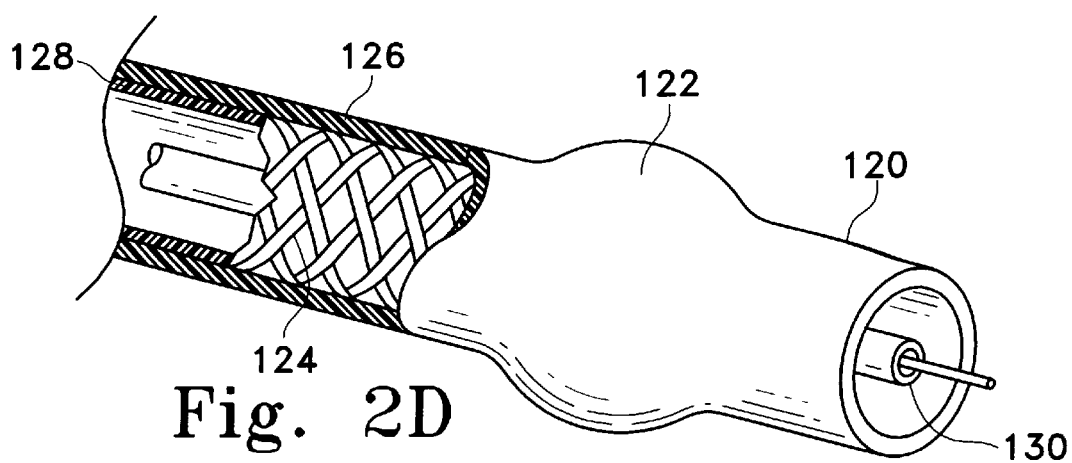

FIG. 2D shows another variation of the tissue removal member (120). In this variation, the tubular portion of the outer member is elastically expandable. This is depicted by the expanded portion (122) shown in FIG. 2D. An expandable outer tubular section is suitable with any of the variations described above. This variation, however, is expandable due to the use of a woven braid (124) and an elastomeric polymer forming the outer layer (126) of the device. An optional inner layer (128) is also depicted in FIG. 2D but an such inner layer (128) is not, obviously, absolutely necessary. It is convenient and desirable, however. FIG. 2D is a partial cutaway.

The expandable tissue removal member shown in FIG. 2D is especially suitable for use with cutting members (and their allied secondary or smaller tubular section (130)) where the cutting member is significantly larger than the diameter of the outer tubing member. The whole cutting member and inner tubing may be urged through this expandable outer section for use at the chosen site.

Figure 3:
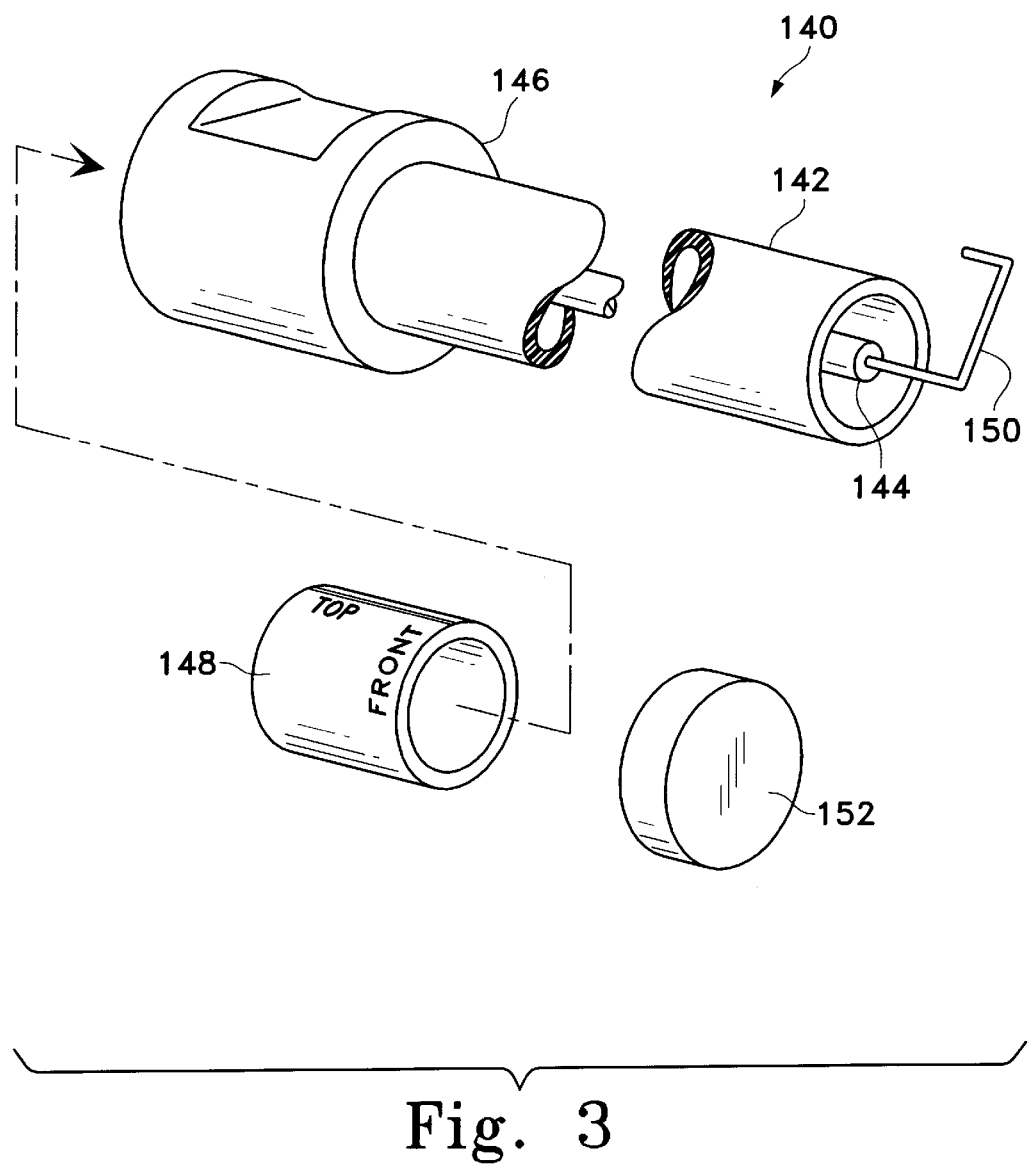
FIG. 3 shows another variation of the tissue removal member, its associated tissue cutting member, and a desirable manner for transporting the accumulated tissue for later analysis.

FIG. 3 shows another variation of the inventive tubular tissue removal member (142), in this instance, having a center small tubing member (144). Of particular instance in this variation is the presence of a receiver (146) situated at the proximal end of the tubular tissue removal member assembly (140).

Of special interest is the specimen collector (148) which may be fitted within receiver (146). It is within the scope of this invention to index the position of the tissue cutting member (150), here depicted as a simple squared-J, with the position of the tissue collector (148) so that as the tissue is removed through the tubular tissue removal member (142), it ultimately resides in the tissue collector (148) in the very position as found in the chosen collection site within the body. A cap (152) for the tissue collector (148) is also shown.

Figure 4A:
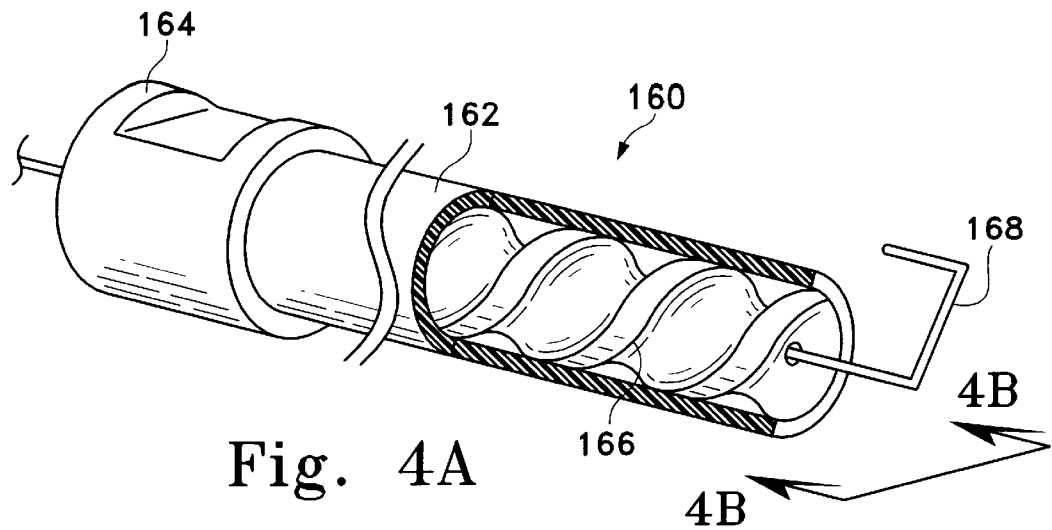
FIGS. 4A and 4B show, respectively, a partial cutaway side view and an end view of a variation of tissue removal member and in particular, show an augering device to assure orderly removal of the excised tissue from the target area.

FIG. 4A shows a variation of the tubular tissue removal member (160) having an outer tubular member (162), an integral receiver (164), and a tissue displacement auger (166).

In this variation of the inventive device, the cutter member (168) rotates in one direction, e.g., clockwise, and the auger (166) rotates in the other direction, counter-clockwise. In this way, the excised tissue leaves the cuting surface as it is separated from the remaining tissue and is newly-deposited in the form as found in the body, in the receiver (164).

In general, the auger (166) maintains the integrity and continuity of the removed tissue by maintaining the separation of the turns of the tissue as it passes from the distal end of the tubular tissue removal member (160) to the proximal end. The auger (166) may be stationary as the cutter advances in the tissue member (168) if the tissue is pulled from the proximal end.

It may be apparent that the tissue removal member (160) may be advanced (or stationary) as the cutting member (168) progresses spirally through the tissue to be excised. In many instances, movement is not necessary, however.

Figure 4B:
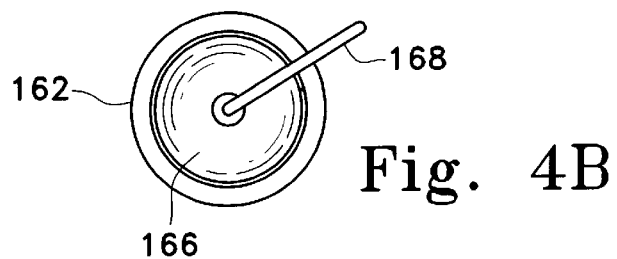

FIG. 4B shows an end view of the device found in FIG. 4A. In it may be seen the cutting member (168); which cutting member has a significantly larger diameter as it rotates than does the inner diameter of tubing member (162). The leading edge of auger (166) may also be seen in FIG. 4B.

Figure 5:
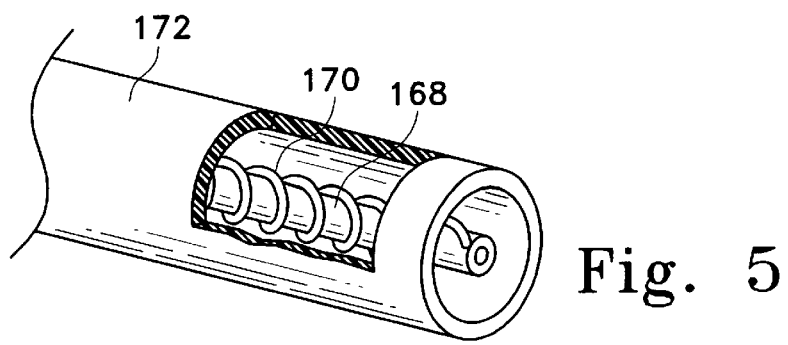
FIG. 5 shows another variation of the tissue auger in partial cutaway side view within the tissue removal member.

The diameter of auger (166) in this instance is fairly close in size to the inner diameter of outer tubing member (162). This tight clearance is not, however, necessary. For instance, FIG. 5 shows a tubular tissue removal member having an auger (168) with vanes (170) having a significantly smaller diameter. Auger (168) provides a significant clearance between the tip of the vanes (170) and the interior lumen of outer tubular member (172). In some instances, it may be desirable to use a smaller diameter auger so to allow for, for instance, a grasping device to slide between the auger and the interior of the wall, to grasp the tissue as it comes off the cutter, and to urge the excised tissue towards the proximal end of the tubular tissue removal member.

TROCAR

The trocar used in this assemblage is preferably one which fits within the inner lumen of the tubular tissue removal member. This permits the trocar to carry that member as it penetrates the outer skin and the tissue on the pathway to the selected site. The trocar used in this invention may simply be one having a sharp mechanical cutting surface or may be connected to one of any of known RF sources which generates energy for cutting tissue and, perhaps, cauterizing it as the initial incision is made.

FIG. 6A shows a typical, but highly desirable, variation of a trocar (200) which is especially suitable for use in this assembly. Specifically, trocar (200) has a sharp leading pointed end (202), a sharp cutting edge (204) and, desirably, a transverse slot (206) for carrying the cutting member to the selected tissue site.

CUTTING MEMBER

The cutting members discussed herein are all similar in that each have a cutting surface, i.e., the portion of the device which meets the tissue and cuts a path whether that path is made by a mechanical cutting as with a knife blade or if the separation is made by an RF or ultrasound energy source. The cutting member may be attached to an RF or ultrasound source or may be made up of mechanical cutters or may be combinations of the those. Often, the members are mechanically vibrated to produce a cutting motion. It is within the scope of this invention that the tissue itself be vibrated to produce a differential motion between the tissue and the cutting surface to create a mechanical cutting motion.

FIGS. 7A, 7B, and 7C schematically depict three shapes especially suitable for use as RF cutters. The tissue cutting member shape (300) shown in FIG. 7A is generally referred to as the "L" shape. The cutting member has a shaft (302) and a radial member (304) and a very short axial cutting length (306). This shape is especially suitable when the pitch of the desired helix made in the chosen tissue, is quite small. The pitch of the cut helix should be no smaller than the length of axial cutting section (306).

FIG. 7B shows a similar cutting member (310) also having a radial cutting surface (312) and an axial cutting surface (314). This shape is known as a "squared-J."

FIG. 7C shows a "rounded-J" shape (316). It also has an axial cutting surface (318). The radial cutting surface (320) is rounded.

Especially suitable for this service is the squared-J shape (322) with a distal extension (324) as shown in FIG. 7D. We have found that occasionally when approaching the boundary of lesions within, e.g., breast tissue, the cutting member variations shown in FIGS. 7A, 7B, and 7C may stray from the directed path. Axial extension (324) serves as a leader or guide and prevents any tendency of the cutter to wander or, indeed, to stop the tissue from being pushed away from the cutter. It is sometimes desirable to insulate the shaft of distal extension (324) distal from the tip so to further stabilize the movement of the distal shaft extension through the perforation or pathway that has been produced by the leading tip (328) of the distal extension.

FIGS. 8A through 11B show shapes which are appropriate for tissue cutting members used in accordance with this invention when RF is applied to the cutter as the cutting energy.

Figure 8A:
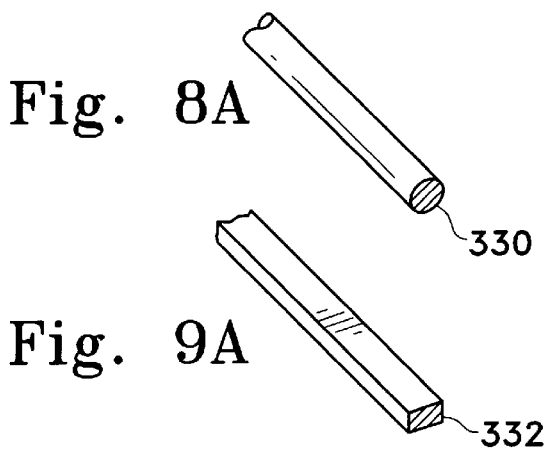

FIGS. 8A and FIG. 8B show a simple round wire for the cutting member. FIG. 9A and 9B show a cutting member having a rectangular cross-section (332). FIGS. 10A and 10B show cross-section (334) having a knife edge (336). A sharpened knife edge such as (336) will focus the RF energy towards the leading edge of the cutting surface and facilitate movement of the device through the tissue. Again, it is within the scope of this invention that this variation of the invention be used as a combination mechanical and RF cutter. Similarly, FIGS. 11A and 11B show a cross-section (338) which also has a serrated knife edge (340). The further limitation of surface area on the leading edge of the cutting member enhances the use of RF in the cutting member of the invented device.

The material making up the cutting members shown in FIGS. 7A through 11B is not central to this invention. The materials may be any of a variety of stainless steels, cobalt alloys, and other alloys typically used in this service.

Nonetheless, we have found that certain titanium-nickel alloys are particularly suitable for use with this device, particularly when the blades are used either as simple knife edge cutters or as a combination of RF/mechanical cutters. This material is typically a 50/50 molar ratio alloy of titanium and nickle. Closely related alloys are the shape memory alloys which exhibit superelastic/pseudoelastic shape recovery characteristics. These alloys are well-known and are commonly referred to as "nitinol." See, for instance, U.S. Pat. Nos. 3,174,851; 3,351,463; as well as 3,753,700. These alloys are characterized by their ability to be transformed from an austenitic crystal structure to a stress-induced martensitic (SIM) structure at certain temperatures, and return elastically to the austenitic shape when the stress is removed. These alternating crystalline properties provide the alloy with its super-elastic properties. The nitinol forms of these alloys are readily commercially available and typically will undergo the austenite-SIM-austenite transformation at a variety of temperature ranges between −20° C. and 30° C.

Figure 12A:
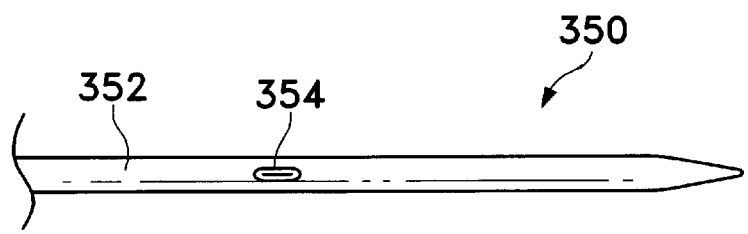
FIGS. 12A to 12B show a two-part expandable diameter cutting member and depict the steps of the cutting surface expansion.
Figure 12B:
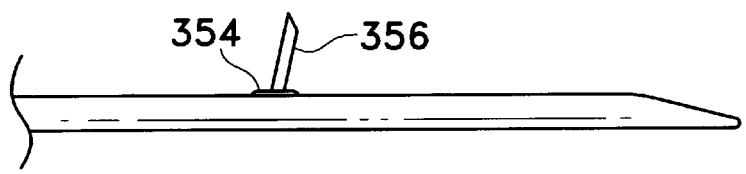
Figure 12C:
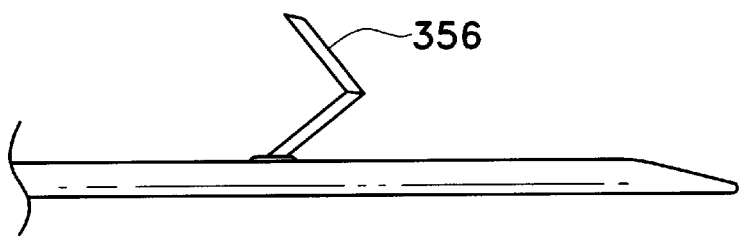
Figure 12D:
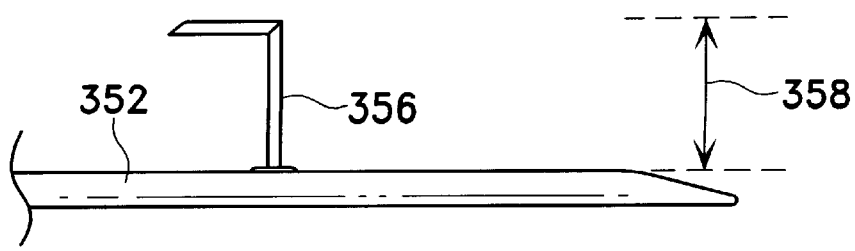

FIGS. 12A through 12D show a cutting member which is extendable from a delivery shape (as shown in FIG. 12A) to a fully extended and deployed shape (as shown in FIG. 12D). The cutting surface of this particular variation is desirably a superelastic alloy because of difficulty of unfolding the device without inducing strain upon the cutting member material.

FIG. 12A shows device as delivered through the small lumen tubular member discussed above. The cutting member assemblage (350) has an outer tubing member (352) and a window (354) for exiting of cutting surface member (356). Cutting member (356) is slideably extendable through the lumen of cutting tubular member (352).

FIG. 12B shows cutting member (356) emerging from window (354).

FIG. 12C shows the further emergence of cutting member (356) and FIG. 12D shows cutting member (356) fully emerged from cutting member shaft (352).

This variation of the invention allows the use of a fairly large diameter cutting member, e.g., one having a cutting radius (358) which is more than the overall outside diameter of the tubular tissue removal member for which it is deployed.

Figure 13A:
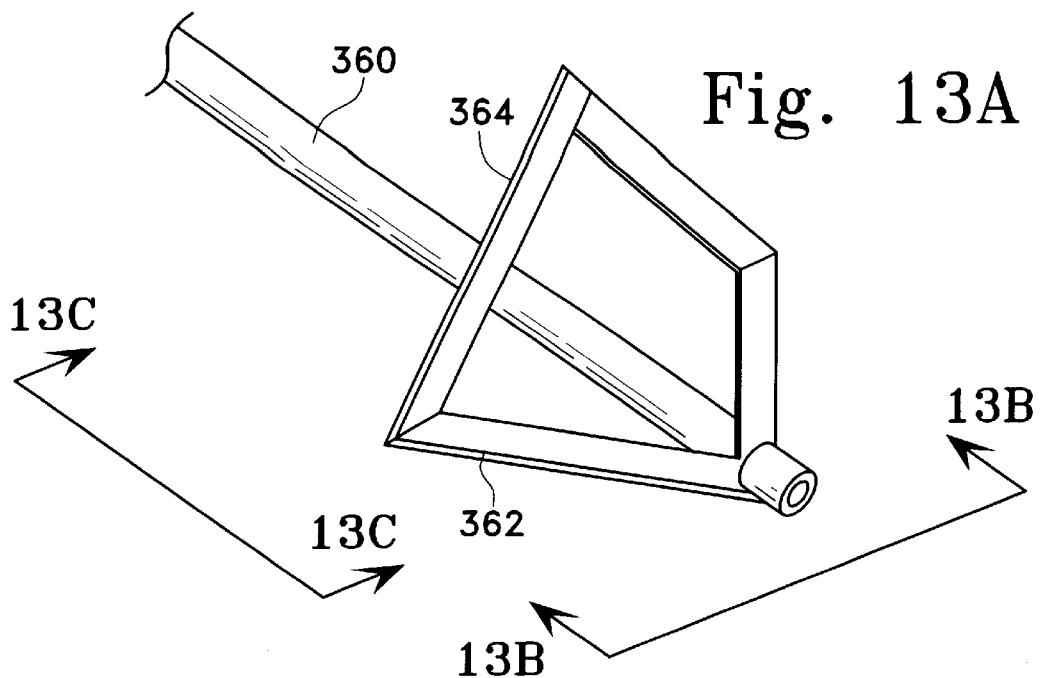
FIG. 13A shows a front quarter view.

FIG. 13A shows a tissue cutting member (360) which is used primarily for mechanical cutting although it obviously may be used as a combination of RF and mechanical cutter as well. We have observed that the tissue found in the breast, cutting is facilitated by using a presenting a cutting surface which is angular to the path of the cutter. That is to say that when cutting a circle in tissue by rotating that cutting member in a circle, a cutting surface which conforms to the radius of cut circle is less effective than one that does not conform to that radius. A cutting surface having a point or peak in it is also desirable.

The cutting member (360) shown in FIG. 13A meets these criteria. Specifically, cutting surface (362) is radius. However, the remaining cutting surface (364) provides an angular surface to the direction of cutting. As noted above, this device may be vibrated or the tissue to be removed may be vibrated to provide additional cutting action.

Figure 13B:
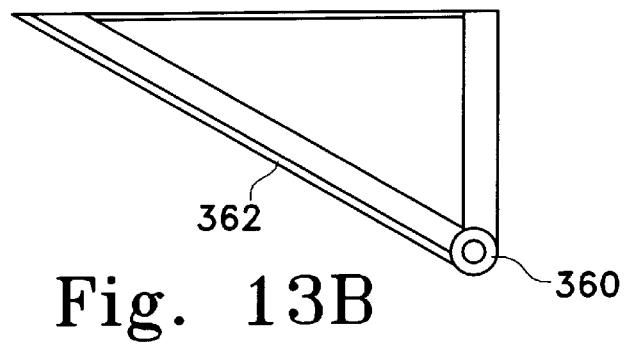
FIG. 13B shows an end view.
Figure 13C:
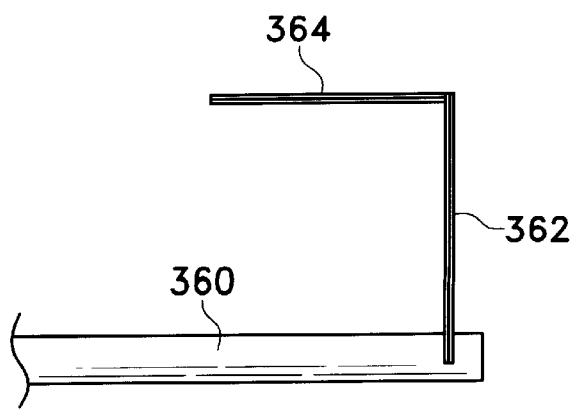
FIG. 13C shows a side view of an extendible mechanical cutting member.

FIG. 13B shows an end view of the cutting member and the end cutting surface (362). FIG. 13C shows a side view of the cutting member (360).

FIG. 14A shows another variation of the mechanical cutting member (370). Each of the radially extending blades (372) and axially extending blades (374) have a triangular shape with a leading edge (376) which are positioned so to present an angular cutting surface to the tissue to be excised. As may be seen in FIGS. 14B and 14C, the triangular cutting blades have points (378) and (380) which serve to enhance the cutting capabilities of the depicted cutting member (370).

Figure 15A:
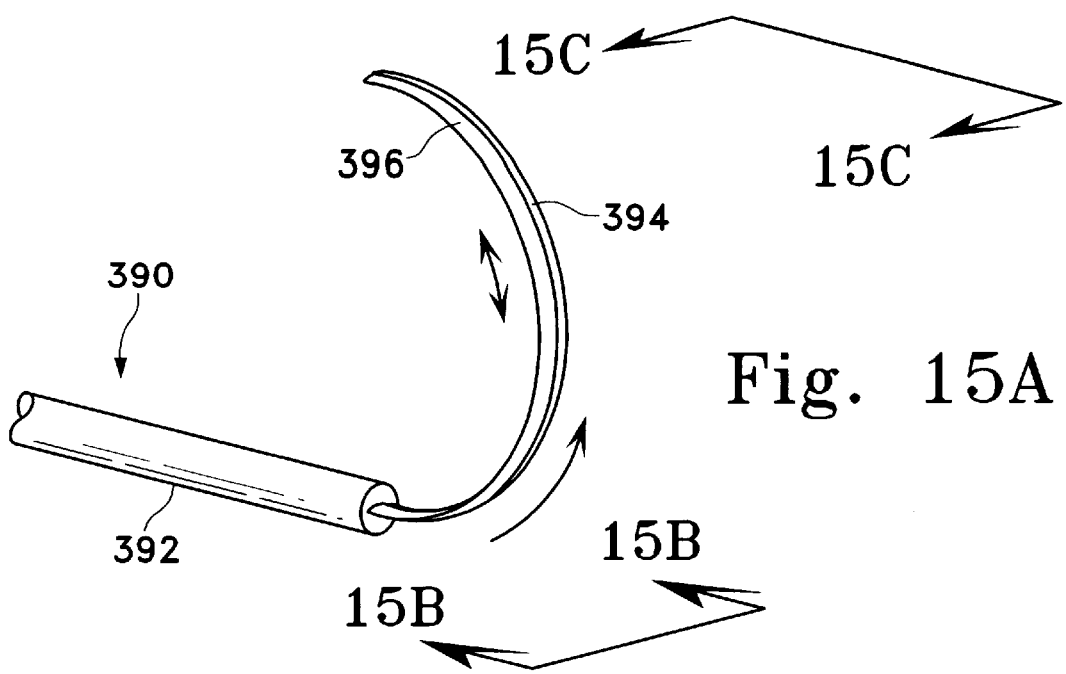
FIG. 15A shows a front quarter view.

FIGS. 15A through 15D show an extendable cutting member (390). The cutting member (390) is made up of three members: a housing member (392), a guide track (394), and a cutting member (396). Guide member (394) and cutting member (396) are shown extended from the housing (392) in each of FIGS. 15A, 15B, and 15C. However, as is noted by the arrow in FIG. 15A, the guide member (394) and cutting member (396) are extended from the housing. Such extensions are done upon arrival of the device at the selected excision area. Desirably, the blade or cutting member (396) is made of a sharpened super-elastic alloy of the type discussed above. Similarly, a guide member (394) is also so constructed. This allows the blade and guide to be extended from the housing (392) and retain a desired shape upon that extension. The blade member (396) is desirably oscillated in a saw-like fashion as depicted in FIG. 15A as shown by the arrows in FIG. 15A.

Figure 15D:
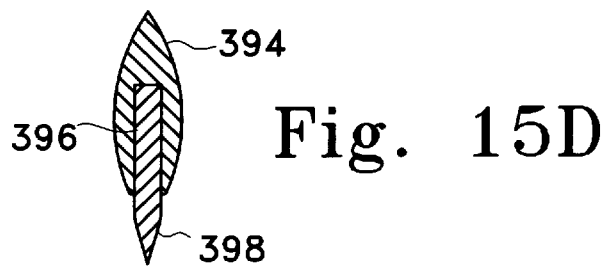
FIG. 15D shows a typical cross-section of the two part cutting surface.
Figures 15B, 15C:
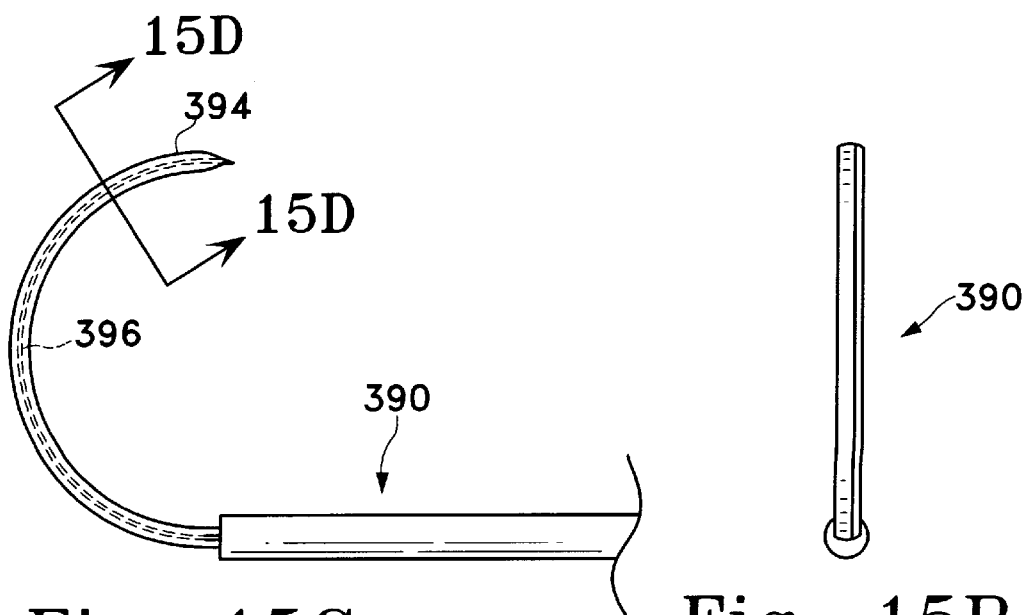
FIG. 15B shows an end view.
FIG. 15C shows a side view of a cutting member having a two-part cutting surface which is extendable from the shaft of the cutting member.

FIG. 15B shows an end view of the cutting member. FIG. 15C shows a side view of the tissue cutting member (390). It may be observed that the tip of cutting member (396) is extendable past the tip of carrier (394). This allows a cut to be made during each bit of the oscillatory travel of cutting blade (396).

FIG. 15D shows, in cross-section, the relationship between carrier (394) and cutting blade (396). The cutting surface (398) is also depicted in this cross-sectional view.

The tissue mass removed by this curved blade is obviously not a cylindrical section as that term is used with respect to the devices and variations found above. The section or mass removed by this variation of the invention is respectively concave at one end and convex at the other. Nevertheless, other shapes which are deployable in this fashion are also contemplated.

Figure 16:
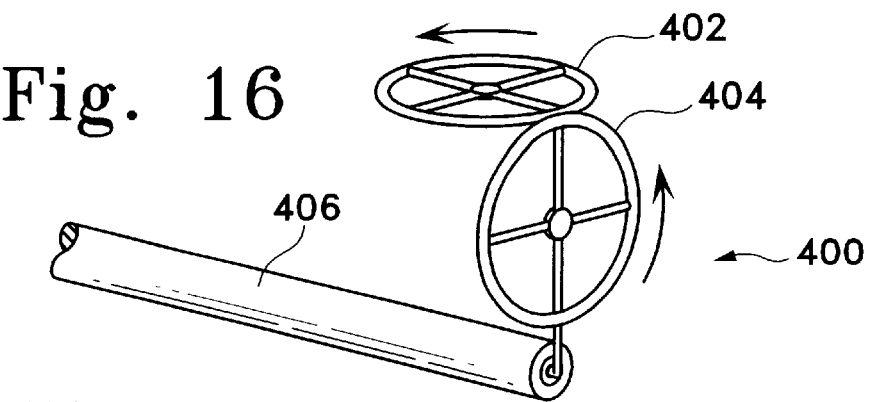
FIG. 16 shows a variation of the cutting member in which a mechanical cut is made using rotating, generally circular, blades.

FIG. 16 shows a version of the invention (400) which the axial cutting members (402) and the radial cutting member (404) are moving as by rotating. Shaft (406) contains a small drive cable which engages a hub on the rotating blades (402) and (404).

Figure 17A:
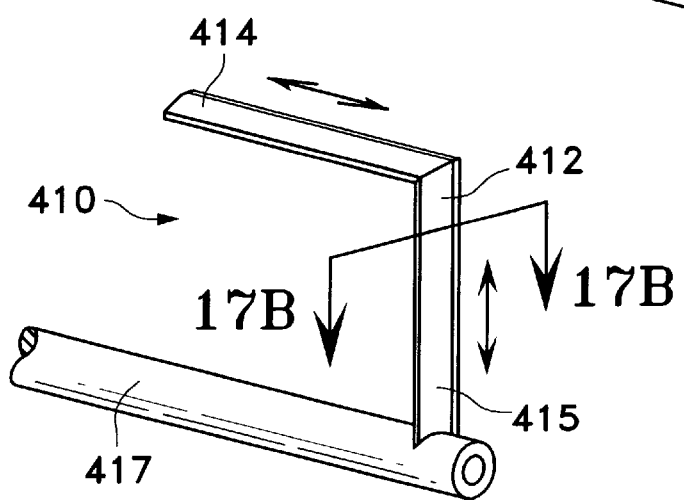
FIG. 17A is a front quarter view of a cutting member having a single leading cutting surface.
Figure 17B:
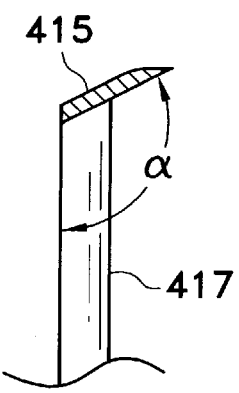
FIG. 17B is a cross-sectional view of the radial blade of the cutting member shown in FIG. 17A showing the cutting angle.

FIG. 17A depicts a tissue cutting member (410) having a straightforward radial cutting blade (412) and an axial cutting blade (414). The variation depicted in FIG. 17 may be oscillated to enhance its cutting capabilities or may be imbued with RF or ultrasound energy as well. FIG. 17B shows a cross-section of the device shown in FIG. 17A. The desired angle (α) of cutting blade (415) as mounted on shaft (417). Some thought should be given in selecting the value of angle (α). It may range in value from 0° to 75° or so depending upon physical considerations such as, e.g., the size of the large lumen in the tissue removal member the smaller the lumen, the thinner the tissue spiral should be, the smaller the angle (α) should be.

Figure 18A:
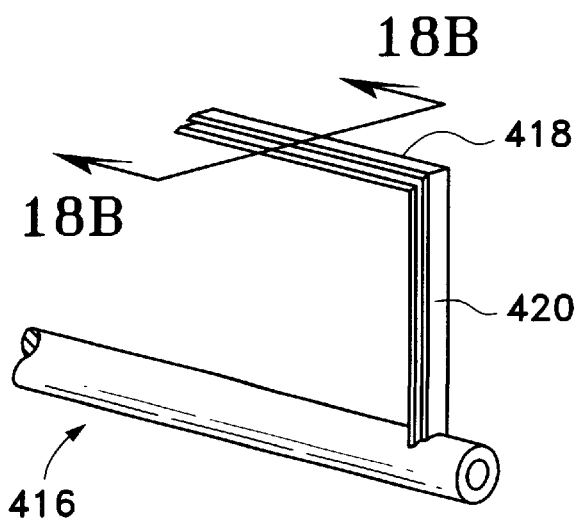
FIG. 18A is a front quarter view of a multiple blade, rotatable cutting member
Figure 18B:
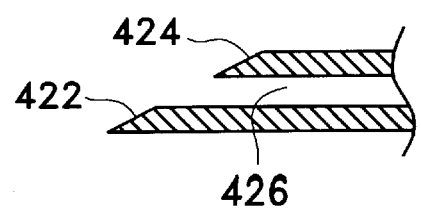
FIG. 18B is a partial cross-sectional view of the cutting surfaces for that cutting member.

FIGS. 18A and 18B show a variation of the cutting member (416) which includes a double-bladed cutting surface on both the axial cutting member (418) and the radial cutting member (420). This variation, the details of the cross-section of which are better depicted in FIG. 18B, has a leading cutting surface (422) trailing cutting surface (424). They are separated by a modest gap (426). The trailing blade (424) widens the adverse angle at which the leading blade (422) meets the tissue to be removed.

TISSUE MANIPULATION DEVICES

Figure 19A:
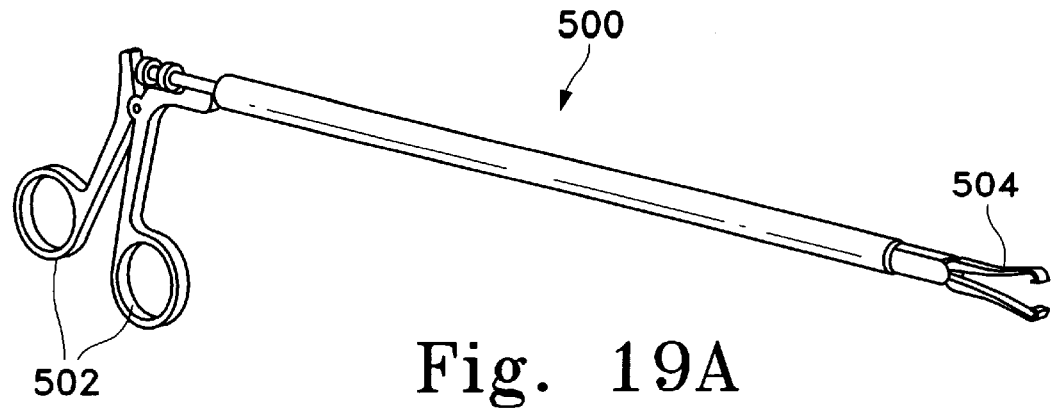
FIG. 19A is a side view of a typical endoscopic snare suitable for use in grasping the removed tissue in accordance with this invention.
Figure 19B:
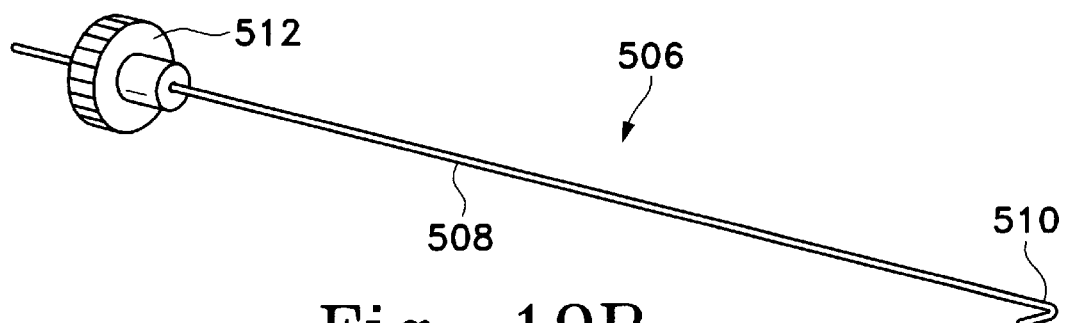
FIG. 19B shows a harpoon spear which is also suitable for accessing and grabbing tissue for use in removing selected tissue when using this device.
Figure 19C:
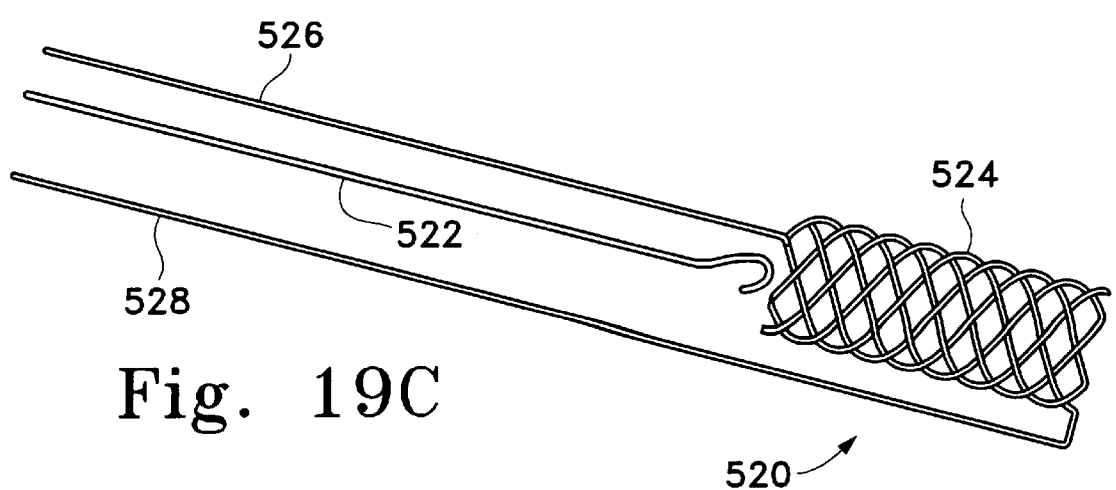
FIG. 19C is an expandable braid and optional allied hook also suitable for retrieving tissue using this invention.

FIGS. 19A through 19C show tissue manipulation devices as may be used in conjunction with the overall assembly. In some instances, it may be desirable to grasp the initial portion of excised tissue so to guide it through the tissue removal member. Depending on which of the configurations of tissue removal member is selected, a choice of one of the noted devices may be appropriate.

FIG. 19A shows a simple endoscopic grasping device (500) which is readily available on the commercial market. Movement of the scissor-like handle produces a corresponding movement on the grasping tongs (504).

FIG. 19B shows a tissue manipulation device (506) having a small wire-like shaft (508) and a harpoon-like end (510). For the purposes of completeness only, a manipulation knob (512) is also included for view. This variation (506) is significantly flexible and may be used in, e.g., the auger tissue removal devices described above to ensure that the tissue in fact engages the interior of the auger and is removed as the auger turns.

FIG. 19C shows a combination of braided grasper (520) and a hook component (522). The braided tissue snaring device (520) includes a distal woven braid section (524) which is easily manipulated by the two control wire or rods (526) and (528). If necessary, hook (522) is used to pull the excised tissue into braided cage (524). The two control wires (526) and (528) are used to either expand the diameter of braided cage (524) or to make that diameter smaller. Once the tissue is at least partially within the braided cage (524), the device is removed from the lumen of the tissue removal device.

Other devices for removing excise tissue from the selected site would certainly be appropriate.

PROCEDURE FOR USE

FIGS. 20A through 20G show a generic method for using the tissue removal assembly of this invention. For the purposes of description here, this description assumes that the user is removing a lesion found in breast tissue. The lesion (600) is found behind skin surface (602). Surrounding tissue is also shown. The generic device found in FIG. 1 is used for purposes of this description. The use, however, according to this invention is not significantly different when other variations of the device are used.

Figure 20A:
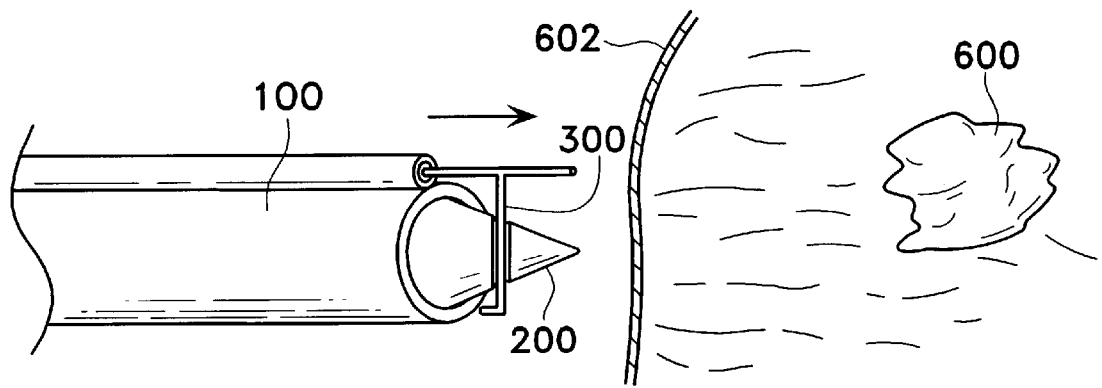
FIGS. 20A through 20G show a typical procedure sequence using the invention described herein and, in particular, the kit selection found in FIG. 1.
Figure 20B:
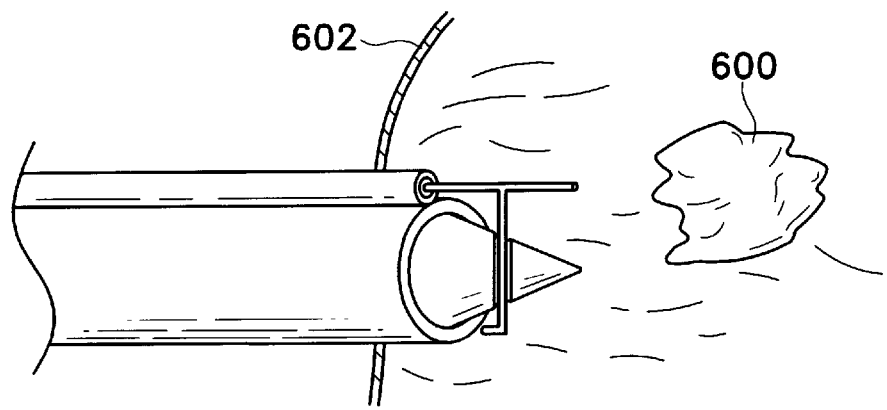

FIG. 20A shows the assembled device ready for introduction to the skin surface. Shown is the tissue removal member (100) and trocar (200) with the nestled cutting member (300) residing in the transverse slot found in trocar (200). The device is positioned at the skin surface so that when a complete rotation of the cutting member (300) is had, the lesion (600) is within that circumference. FIG. 20B shows the assembled device after it has penetrated the skin surface (602) and is approaching lesion (600).

Figure 20C:
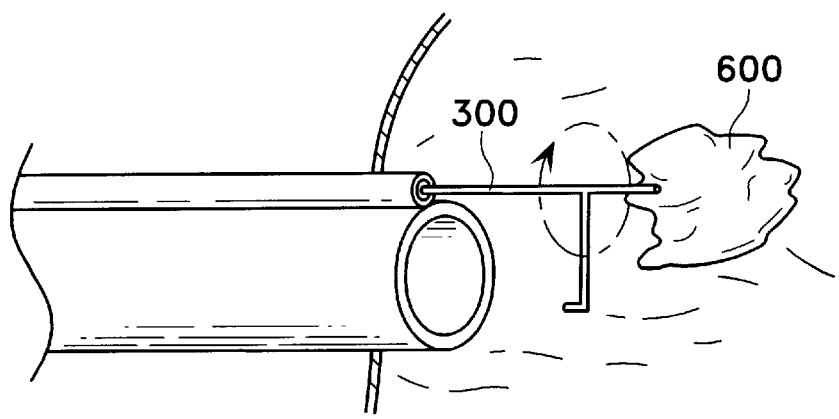

FIG. 20C shows the initial entry of the cutting member (300) into lesion (600). This variation shows the use of an RF powered cutting member (300). A mechanical or ultrasound cutter may obviously be employed as well or instead of an RF style cutter (300). The cutting member (300) is first rotated so to form a circular cut distally of lesion (600). This circular cut will be the end of the cylinder of tissue which is ultimately removed.

Figure 20D:
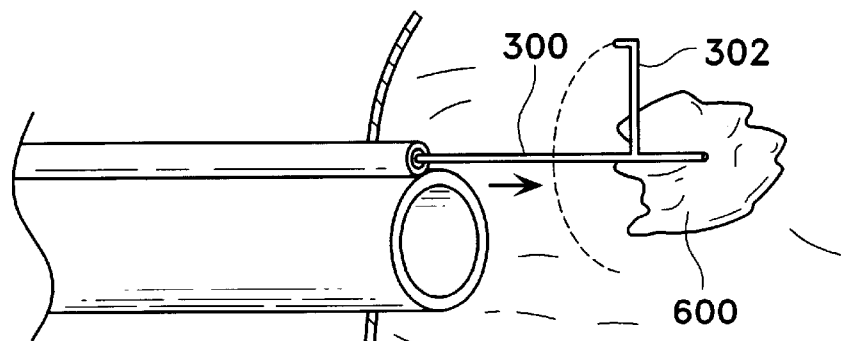

FIG. 20D then depicts the axial movement of the cutting member (300) and the spiral shape of the cut as the cutting member (300) is rotated until the axial portion (802) is past lesion (600).

Figure 20E:
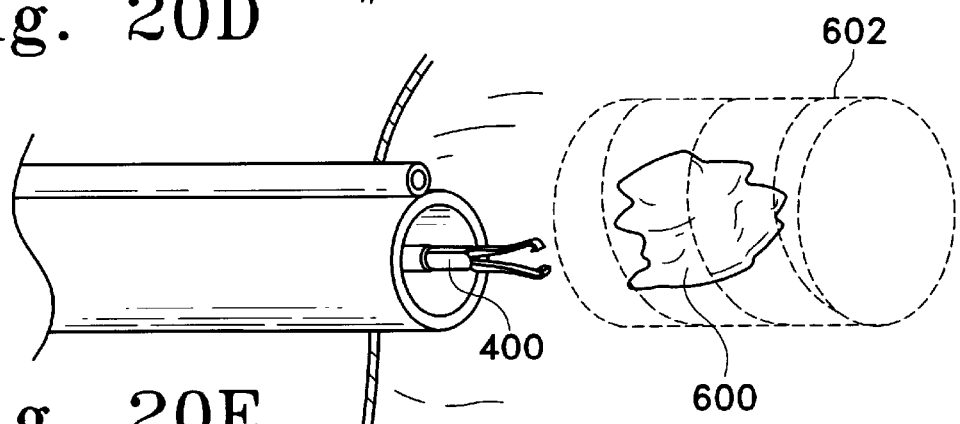

FIG. 20E shows the introduction of grasping member (400) to the distal end of the cylindrical tissue mass (602) containing lesion (600).

Figure 20F:
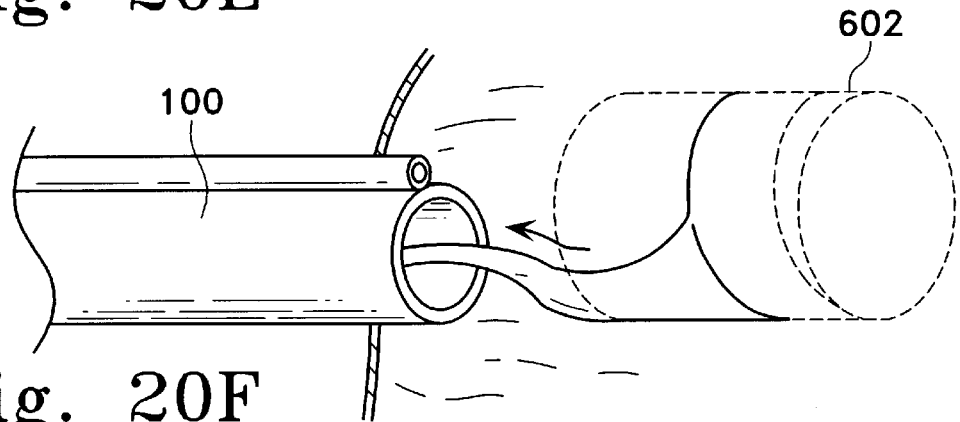

FIG. 20F shows the removal of the helically cut tissue of cylindrical tissue mass (602) through the large lumen of tissue removal of member (100). The large lumen may be used to pack the remaining cavity with, e.g., inert packing material such as carbon.

Figure 20G:
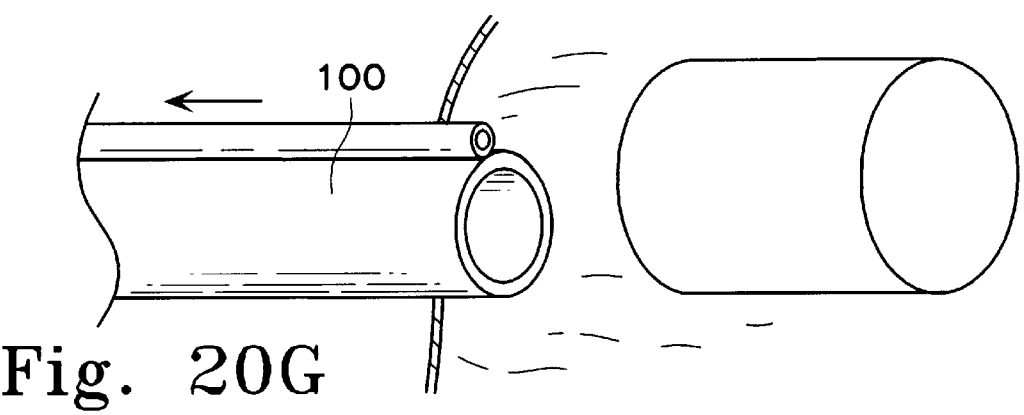

FIG. 20G shows the removal of tissue removal member (100) from the breast.

The invention herein has been described by examples and a particularly desired way of practicing the invention has been described. However, the invention as claimed herein is not loaded to that specific description in any manner. Equivalence to the description as hereinafter claimed is considered to be within the scope of protection of this patent.

We claim as our invention:

1. A tissue removal assembly, comprising:
    a.) a tubular tissue removal member having a wall, a distal diameter, a proximal end, a distal end, and a longitudinal axis extending between said proximal end and said distal end; an open, distally located tissue entry opening; a relatively more proximal, tissue exit port; and a tissue removal passageway extending between said tissue entry opening and said tissue exit port;
    b.) a cutting member having a generally rounded "J" shape, a generally square "J" shape, or an "L" shape, said cutting member being rotatable with respect to said tubular tissue removal member in a diameter greater than the tubular tissue removal member distal diameter, extendible beyond said distally located tissue entry opening, and having a cutting surface, where upon rotation of said cutting member and extension of said cutting member distally beyond said tissue entry opening within a tissue region, said cutting surface cuts a discrete tissue mass having an overall diameter measured generally orthogonal to the tubular tissue removal member axis which is greater than said tubular tissue removal member distal diameter and which discrete tissue mass is in a configuration removable through said tissue entry opening.

2. The tissue removal assembly of claim 1 wherein said cutting surface is configured to cut a radial, helical path through discrete tissue mass.

3. The tissue removal assembly of claim 1 wherein said cutting member is manually manipulatable from the proximal end of said tubular tissue removal member.

4. The tissue removal assembly of claim 1 wherein said cutting member has an axis of rotation and a distal extention along said axis of rotation.

5. The tissue removal assembly of claim 1 wherein said cutting member is at least partially radio-opaque.

6. The tissue removal assembly of claim 4 wherein said cutting member is at least partially radio-opaque.

7. The tissue removal assembly of claim 4 wherein said cutting member distal extension is at least partially radio-opaque.

8. The tissue removal assembly of claim 1 wherein said cutting member is a wire cutting member.

9. The tissue removal assembly of claim 1 wherein said cutting member is a ribbon cutting member.

10. The tissue removal assembly of claim 1 wherein said cutting member comprises a material selected from the group consisting of titanium, nickel, stainless steel, cobalt, tantalum, and nickel and mixture and alloys of thereof.

11. The tissue removal assembly of claim 1 wherein said cutting member comprises titanium and nickel.

12. The tissue removal assembly of claim 1 wherein said cutting member is an RF cutter utilizing radio-frequency energy to cut said discrete tissue mass.

13. The tissue removal assembly of claim 12 further comprising an RF source connected to said cutting member which is suitable for cutting said discrete tissue mass.

14. The tissue removal assembly of claim 1 wherein said cutting member is a mechanical blade.

15. The tissue removal assembly of claim 14 wherein said mechanical blade cutting member is vibrated.

16. The tissue removal assembly of claim 1 wherein said cutting member is an RF cutter having a sharp mechanical cutting surface.

17. The tissue removal assembly of claim 1 wherein said cutting member is an ultrasound cutter utilizing high frequency audio energy to cut said discrete tissue mass.

18. The tissue removal assembly of claim 17 further comprising an ultrasound source connected to said cutting member which is suitable for cutting said discrete tissue mass.

19. The tissue removal assembly of claim 1 wherein said tubular tissue removal member further includes a shaft passageway exterior to said tissue removal passageway and generally parallel to said tubular tissue removal member longitudinal axis and said cutting member includes a shaft extending between said cutting surface and said tubular tissue removal member proximal end and is slideable within and rotatable within said shaft passageway to advance said cutting surface.

20. The tissue removal assembly of claim 1 wherein said tubular tissue removal member further includes a shaft passageway interior to said tissue removal passageway and generally parallel to said tubular tissue removal member longitudinal axis and said cutting member includes a shaft extending between said cutting surface and said tubular tissue removal member proximal end and is slideable within and rotatable within said shaft passageway to advance said cutting surface.

21. The tissue removal assembly of claim 1 further comprising a pick locatable within said tissue removal passageway which pick is configured for removing said discrete tissue mass.

22. The tissue removal assembly of claim 1 further comprising a manipulatable grasping tool locatable within said tissue removal passageway which grasping tool is configured for removing said discrete tissue mass.

23. The tissue removal assembly of claim 22 wherein said manipulatable grasping tool comprises a pair of opposing jaws suitable for grasping said discrete tissue mass.

24. The tissue removal assembly of claim 22 wherein said manipulatable grasping tool comprises a grasping braid suitable for grasping said discrete tissue mass.

25. The tissue removal assembly of claim 1 further comprising a manipulatable suction tool locatable within said tissue removal passageway which suction tool is configured for removing said discrete tissue mass.

26. The tissue removal assembly of claim 1 further comprising a trocar sized to fit within said tissue removal passageway.

27. The tissue removal assembly of claim 26 wherein said trocar includes a leading cutting edge and a slot in said leading cutting edge and said cutting surface fits in said trocar slot.

28. The tissue removal assembly of claim 26 wherein said trocar is extendible distally though said tissue entry opening.

29. The tissue removal assembly of claim 1 wherein said tissue entry opening is open along the axis of said tubular tissue removal member.

30. The tissue removal assembly of claim 1 wherein said tissue entry opening is open generally perpendicular to the axis of said tubular tissue removal member.

31. The tissue removal assembly of claim 1 further comprising a rotatable auger situated within said tubular tissue removal member for moving excised tissue along said tubular tissue removal member to said tissue exit port.

32. A procedure for removing tissue from a selected internal tissue region, comprising the steps of:

introducing a tissue removal assembly to a region adjacent a selected internal tissue region, said tissue removal assembly comprising:

a.) a tubular tissue removal member having a wall, a distal diameter, a proximal end, a distal end and a longitudinal axis extending between said proximal end and said distal end; an open, distally located tissue entry opening; a relatively more proximal, tissue exit port; and a tissue removal passageway extending between said tissue entry opening and said tissue exit port, b.) a cutting member having a generally rounded "J" shape, a generally square "J" shape, or an "L" shape, said cutting member being rotatable with respect to said tubular tissue removal member in a diameter greater than the tubular tissue removal member distal diameter, extendible beyond said distally located tissue entry opening, and having a cutting surface, where upon rotation of said cutting member and extension of said cutting member distally beyond said tissue entry opening within said tissue region, said cutting surface cuts a discrete tissue mass having an over all diameter measured generally orthogonal to the tubular tissue removal member axis which is greater than said tubular tissue removal member distal diameter and which discrete tissue mass is in a configuration removable through said tissue entry opening, rotating said cutting member and said cutting surface to form a discrete tissue mass having an overall diameter measured generally orthogonal to the tubular tissue removal member axis which is greater than said tubular tissue removal member distal diameter and which discrete tissue mass is in a configuration removable through said tissue entry opening, and removing said discrete tissue mass through said tissue entry opening, through said tissue removal passageway, and out through said tissue exit port.

33. The procedure of claim 32 wherein the cutting member is rotated to form a helical cut in said discrete tissue mass.

34. The procedure of claim 32 wherein said cutting member has an axis of rotation and a distal extension along said axis of rotation.

35. The procedure of claim 32 wherein said cutting member is at least partially radio-opaque.

36. The procedure of claim 32 wherein said cutting member is a wire cutting member.

37. The procedure of claim 32 wherein said cutting member comprises a material selected from the group consisting of titanium, nickel, stainless steel, cobalt, tantalum, and nickel and mixture and alloys of thereof.

38. The procedure of claim 37 wherein said cutting member comprises titanium and nickel.

39. The procedure of claim 32 wherein said cutting member is an RF cutter utilizing radio-frequency energy to cut said discrete tissue mass and wherein said step of rotating said cutting member and said cutting surface to form a discrete tissue mass includes the imposition of radio-frequency energy to effectuate said cutting.

40. The procedure of claim 32 wherein said cutting member is a mechanical blade.

41. The procedure of claim 40 wherein said mechanical blade cutting member is vibrated.

42. The procedure of claim 32 wherein said cutting member is a is an RF cutter having a sharp with mechanical cutting surface.

43. The procedure of claim 32 wherein said cutting member is an ultrasound cutter utilizing high frequency audio energy to cut said discrete tissue mass and further including the step of applying ultrasound energy to said cutting member.

44. The procedure of claim 32 wherein said trocar includes a leading cutting edge and a slot in said leading cutting edge and said cutting surface fits in said trocar slot.

45. The procedure of claim 32 wherein said tissue removal assembly further comprises a rotatable auger situated within said tubular tissue removal member for moving excised tissue along said tubular tissue removal member to said tissue exit port and wherein said procedure includes rotating said auger to remove excised tissue.

46. The procedure of claim 45 further comprising the step of reconstituting the excised tissue to the form as found prior to the cutting step.

\* \* \* \* \*

UNITED STATES PATENT AND TRADEMARK OFFICE
CERTIFICATE OF CORRECTION

PATENT NO.   : 6,136,014
DATED        : October 24, 2000
INVENTOR(S)  : D. Laksen Sirimanne, et al.

It is certified that error appears in the above-identified patent and that said Letters Patent is hereby corrected as shown below:

Title page,
Item [56] References Cited, insert: U.S. Patent Documents
| | | |
|---|---|---|
| 2,729,210 | 01/03/56 | Spencer |
| 3,175,554 | 03/30/65 | Stewart |
| 3,732,858 | 05/15/73 | Banko |
| 4,461,305 | 07/24/84 | Cibley |
| 5,611,803 | 03/18/97 | Heaven et al. |
| 5,772,676 | 06/30/98 | Cushieri et al. |
| 5,794,626 | 08/18/98 | Kieturakis |
| 5,810,806 | 09/22/98 | Ritchart et al. |
| 5,913,857 | 06/22/99 | Ritchart et al. |
| 6,007,495 | 12/28/99 | Matula |
| 6,022,362 | 02/08/00 | Lee et al. |

Foreign Patent Documents
| | | |
|---|---|---|
| WO 95/08291 | 03/30/95 | PCT |
| WO 98/08441 | 03/05/98 | PCT |
| 0829232 | 03/18/98 | Europe |

Signed and Sealed this

Eighteenth Day of September, 2001

Attest:

NICHOLAS P. GODICI
Attesting Officer    Acting Director of the United States Patent and Trademark Office